(12) United States Patent
Hagiwara et al.

(10) Patent No.: US 7,649,972 B2
(45) Date of Patent: Jan. 19, 2010

(54) X-RAY CT DATA ACQUISITION METHOD AND X-RAY CT APPARATUS

(75) Inventors: Akira Hagiwara, Tokyo (JP); Kenichi Nishizawa, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 228 days.

(21) Appl. No.: 11/763,810

(22) Filed: Jun. 15, 2007

(65) Prior Publication Data

US 2007/0291894 A1 Dec. 20, 2007

(30) Foreign Application Priority Data

Jun. 20, 2006 (JP) ............... 2006-169616

(51) Int. Cl.
 *A61B 6/00* (2006.01)
(52) U.S. Cl. ............................. 378/4; 378/15
(58) Field of Classification Search ...... 378/4, 378/15
 See application file for complete search history.

(56) References Cited

U.S. PATENT DOCUMENTS

| | | | | |
|---|---|---|---|---|
| 4,789,929 | A | * | 12/1988 | Nishimura et al. ............ 378/15 |
| 5,224,135 | A | * | 6/1993 | Toki ............................. 378/4 |
| 5,278,884 | A | * | 1/1994 | Eberhard et al. .............. 378/4 |
| 5,463,666 | A | * | 10/1995 | Eberhard et al. .............. 378/4 |
| 5,751,782 | A | * | 5/1998 | Yoshitome ................. 378/98.5 |
| 5,784,481 | A | * | 7/1998 | Hu ............................. 382/131 |
| 6,154,515 | A | * | 11/2000 | Lin et al. ....................... 378/4 |
| 6,430,253 | B1 | | 8/2002 | Oikawa |
| 6,907,100 | B2 | * | 6/2005 | Taguchi ....................... 378/4 |
| 6,907,102 | B1 | * | 6/2005 | Sauer et al. ................. 378/19 |
| 6,925,141 | B2 | | 8/2005 | Bruder et al. |
| 6,931,094 | B2 | | 8/2005 | Li |
| 7,173,997 | B2 | | 2/2007 | Hagiwara |
| 2002/0037068 | A1 | * | 3/2002 | Oikawa ....................... 378/15 |
| 2003/0031290 | A1 | * | 2/2003 | Sugihara et al. ............. 378/15 |
| 2003/0076991 | A1 | | 4/2003 | Nishide |
| 2004/0028265 | A1 | | 2/2004 | Nishide |

(Continued)

FOREIGN PATENT DOCUMENTS

JP 2001-112747 4/2001

(Continued)

OTHER PUBLICATIONS

"Oplus E"; New Technological Communications Inc.; Nov. 1988; 3 pgs.

*Primary Examiner*—Edward J Glick
*Assistant Examiner*—Alexander H Taningco
(74) *Attorney, Agent, or Firm*—Armstrong Teasdale LLP

(57) ABSTRACT

The present invention provides a method for positively acquiring projection data for reconstructing a CT image at a slice position outside the linear movement range. When performing "projection data acquisition" with "rotating" and "linearly moving" the X-ray tube and the multidetector, a holding time is provided in which only the "rotation" is performed without "linear movement" at the starting point and the end point of the linear movement. By adjusting the holding time, the projection data in the view angle range required for image reconstruction of a CT at the slice position outside the linear movement range can be positively acquired, when the rotating velocity is slower or when the linear movement velocity is faster.

9 Claims, 6 Drawing Sheets

U.S. PATENT DOCUMENTS

| | | |
|---|---|---|
| 2005/0008116 A1 | 1/2005 | Nishide et al. |
| 2005/0094761 A1* | 5/2005 | Hagiwara .................... 378/15 |
| 2005/0175139 A1 | 8/2005 | Horiuchi et al. |
| 2006/0140478 A1 | 6/2006 | Nishide |
| 2007/0019851 A1 | 1/2007 | Nishide et al. |

FOREIGN PATENT DOCUMENTS

| | | |
|---|---|---|
| JP | 2002095655 | 4/2002 |
| JP | 2005137389 | 6/2005 |
| JP | 2005137389 A * | 6/2005 |

* cited by examiner

X-RAY CT DATA ACQUISITION METHOD AND X-RAY CT APPARATUS

CROSS REFERENCE TO RELATED APPLICATIONS

This application claims the benefit of Japanese Patent Application No. 2006-169616 filed Jun. 20, 2006.

BACKGROUND OF THE INVENTION

The present invention relates to an X-ray CT (computed tomography) data acquisition method and an X-ray CT apparatus, more specifically to an X-ray CT data acquisition method and an X-ray CT apparatus which allows projection data to be acquired for reconstructing a CT image at a slice position outside the linear displacement range in for example the helical scan, the helical shuttle, and the variable helical pitch scan.

There is already known an X-ray CT imaging method for reconstructing an image at a slice position outside the linear displacement range in the helical scan, i.e., relative displacement range in the direction of helical axis with respect to the imaging object of the X-ray tube (for example, see patent JP-A-2005-137389).

To reconstruct a CT image, the projection data of the view angle range over 360 degrees in the full reconstruction mode is required, and the projection data of the view angle range over 240 degrees, for example, in the half reconstruction mode is required.

However, in the Prior Art described above, the rotating movement and the linear movement are started and terminated at the same time at the starting point and at the end point of the linear movement. There arose a problem that, if either the rotating velocity is too slow or the linear movement velocity is too fast, acquirable position may be passed over before acquiring the projection data of the view angle range required to reconstruct the CT image at the slice position outside the linear movement range.

The object of the present invention therefore is to provide an X-ray CT data acquisition method and an X-ray CT apparatus which positively acquire the projection data for reconstructing the CT image at the slice position outside the linear movement range in such scan method as the helical scan, the helical shuttle, and the variable helical pitch scan.

SUMMARY OF THE INVENTION

In a first aspect, the present invention provides an X-ray CT data acquisition method, which comprises a step of providing, when performing a scan for acquiring projection data by performing a linear movement relative to an imaging object while rotating at least one of an X-ray tube or a multidetector relatively around the imaging object, a holding time τ in which the relative rotation is performed while the relative linear movement is not performed at the starting point and the end point of the linear movement.

In the composition described above, the term "relative rotation" includes, in the state of placing an imaging object between an X-ray tube and a multidetector, cases of rotating at least one of the X-ray tube and the multidetector around the imaging object without rotating the imaging object, rotating the imaging object around its body axis without rotating the X-ray tube and the multidetector, and rotating the imaging object around its body axis and rotating at least one of the X-ray tube and the multidetector around the imaging object in the opposite direction, and so on.

In the composition described above, the term "relative linear movement" includes, in the state of placing the imaging object between the X-ray tube and the multidetector, cases of linearly moving (a table carrying) the imaging object but not linearly moving the X-ray tube and the multidetector, linearly moving the X-ray tube and the multidetector but not linearly moving (the table carrying) the imaging object, linearly moving (the table carrying) the imaging object and linearly moving the X-ray tube and the multidetector in the opposite direction, and so on.

In the X-ray CT data acquisition method in accordance with the first aspect described above, a holding time τ is provided at the starting point and the end point of the linear movement, during which time the rotation is performed while the linear movement is not performed. By adjusting the holding time τ, even if the revolving velocity is too slow or the linear movement velocity is too fast, the projection data in the view angle range required for reconstructing the CT image at the slice position outside the linear movement range may be positively acquired.

In a second aspect, the present invention provides an X-ray CT data acquisition method in accordance with the first aspect, in which the holding time τ relies on the velocity V of the relative linear movement.

Depending on the velocity V of the linear movement, the time spent to pass over the position for acquiring the projection data in the view angle range required for the image reconstruction may vary.

Therefore in the X-ray CT data acquisition method in accordance with the second aspect described above, the holding time τ is adjusted in response to the velocity V of the linear movement. In this manner the projection data in the view angle range required for the image reconstruction may be positively acquired, when the velocity V of the linear movement changes.

In a third aspect, the present invention provides an X-ray CT data acquisition method in accordance with the second aspect, wherein the holding time τ2 in the case where the velocity V of the relative linear movement is a value V2 larger than a value V1 is set longer than the holding time τ1 in the case where the velocity V of the relative linear movement is the value V1.

The position for acquiring the projection data in the view angle range required for the image reconstruction is passed faster as the velocity V of the linear movement is larger.

Therefore, in the X-ray CT data acquisition method in accordance with the third aspect, the holding time τ is set longer when the velocity V of the linear movement is faster. The projection data in the view angle range required for image reconstruction may be thereby positively acquired when the velocity V of the linear movement is much faster.

In a fourth aspect, the present invention provides an X-ray CT data acquisition method in accordance with the first aspect, in which the holding time τ relies on one rotation time R of the relative revolution and the velocity V of the relative linear movement.

The time needed to pass over the position where the projection data in the view angle range required for the image reconstruction can be acquired may vary depending on one rotation time R and the velocity V of linear movement.

In the X-ray CT data acquisition method in accordance with the fourth aspect described above therefore the holding time τ is adjusted in response to the one rotation time R and the velocity V of the linear movement. The projection data in the view angle range required for image reconstruction may be positively acquired thereby when one rotation time R and the velocity V of the linear movement change.

In a fifth aspect, the present invention provides an X-ray CT data acquisition method in accordance with the fourth aspect, wherein when a value obtained by dividing the holding time τ by the one rotation time R of the relative rotation is the amount of table resting T, the amount of table resting T in the case where the velocity V of the relative linear movement is a value V2 larger than a value V1, is set larger than the amount of table resting T in the case where the velocity V of the relative linear movement is the value V1.

When the one rotation time R is slower, or when the velocity V of the linear movement is faster, the position is past over faster where the projection data in the view angle range required for the image reconstruction can be acquired.

In the X-ray CT data acquisition method in accordance with the fifth aspect described above, the amount of table resting T, which is the value obtained by dividing the holding time τ by the one rotation time R, is set larger when the velocity V of the linear movement is faster. In this manner the projection data in the view angle range required for the image reconstruction may be positively acquired thereby, when the one rotation time R is slower, and the velocity V of the linear movement is faster.

In a sixth aspect, the present invention provides an X-ray CT data acquisition method in accordance with the first aspect described above, wherein when the area where an image outside the linear movement range from the starting point of the linear movement to the end point of the linear movement can be created is defined as an image extension area, the holding time τ relies on the width of the image extension area d.

The time spent for acquiring the projection data in the view angle range required for the image reconstruction may depend on the width of the image extension area d.

In the X-ray CT data acquisition method in accordance with the sixth aspect described above, the holding time τ is adjusted in response to the width of the image extension area d. In this manner the projection data in the view angle range required for the image reconstruction may be positively acquired when the width of the image extension area d changes.

In a seventh aspect, the present invention provides an X-ray CT data acquisition method in accordance with the sixth aspect, wherein the holding time τ2 in the case where the width of the image extension area d is a value d2 larger than a value d1 is longer than the holding time τ1 in the case where the width of the image extension area d is the value d1.

The time spend for acquiring the projection data in the view angle range required for the image reconstruction becomes shorter when the width of the image extension area d becomes larger.

In the X-ray CT data acquisition method in accordance with the seventh aspect described above, the holding time τ is set longer when the width of the image extension area d is larger. The projection data in the view angle area required for the image reconstruction may be positively acquired thereby when the width of the image extension area d is larger.

In a eighth aspect, the present invention provides an X-ray CT data acquisition method in accordance with the first aspect wherein the holding time τ relies on one rotation time R of the relative rotation and the width of the image extension area d.

The time spent for acquiring the projection data in the view angle range required for the image reconstruction may vary depending on the one rotation time R and the width of the image extension area d.

Therefore, in the X-ray CT data acquisition method in accordance with the eighth aspect described above, the holding time τ is adjusted in response to the one rotation time R and the width of the image extension area d. In this manner the projection data in the view angle range required for the image reconstruction may be positively acquired when the one rotation time R and the width of the image extension area d change.

In a ninth aspect, the present invention provides an X-ray CT data acquisition method in accordance with the eighth aspect, wherein when a value obtained by dividing the holding time τ by the one rotation time R of the relative rotation is the amount of table resting T, the amount of table resting T2 in the case where the width of the image extension area d is a value d2 larger than a value d1 is set larger than the amount of table resting T1 in the case where the width of the image extension area d is the value d1.

The time spent for acquiring the projection data in the view angle range required for the image reconstruction becomes shorter when the one rotation time R is slower and when the width of the image extension area d is larger.

Therefore in the X-ray CT data acquisition method in accordance with the ninth aspect described above, the amount of table resting T, which is obtained by dividing the holding time τ by the one rotation time R, is set to a larger value when the width of the image extension area d is larger. In this manner the projection data in the view angle range required for the image reconstruction may be positively acquired when the one rotation time R is slower, and when the width of the image extension area d is larger.

In a tenth aspect, the present invention provides an X-ray CT apparatus, comprising: an X-ray tube; a multidetector; a revolving device for relatively rotating around an imaging object at least one of the X-ray tube and the multidetector; a linear movement device for relatively linearly moving at least one of the X-ray tube and the multidetector from the start point of a relative linear movement to the end point of the relative linear movement with respect to the imaging object; a scanning device for acquiring the projection data by performing only the relative rotation without performing the relative linear movement at the starting point of the relative linear movement and/or at the end point of the relative linear movement and for acquiring the projection data by performing the relative rotation and the relative linear movement; and an image reconstruction device for generating a CT image at a desired image position within the region of interest by using the projection data acquired.

In the X-ray CT apparatus in accordance with the tenth aspect described above, the X-ray CT data acquisition method in accordance with the first aspect can be suitably implemented.

In an eleventh aspect, the present invention provides an X-ray CT apparatus in accordance with the tenth aspect, wherein the holding time τ, which is the time spent for acquiring the projection data by performing the relative rotation without performing the relative linear movement, relies on the velocity V of the relative linear movement.

In the X-ray CT apparatus in accordance with the eleventh aspect described above, the X-ray CT data acquisition method in accordance with the second aspect can be suitably implemented.

In a twelfth aspect, the present invention provides an X-ray CT apparatus in accordance with the eleventh aspect, wherein the holding time τ2 in the case where the velocity V of the relative linear movement is a value V2 larger than a value V1 is set longer than the holding time τ1 in the case where the velocity V of the relative linear movement is the value V1.

In the X-ray CT apparatus in accordance with the twelfth aspect described above, the X-ray CT data acquisition method in accordance with the third aspect can be suitably implemented.

In a thirteenth aspect, the present invention provides an X-ray CT apparatus in accordance with the tenth aspect, wherein the holding time τ, which is the time spent for acquiring the projection data by performing only the relative rotation without performing the relative linear movement, relies on the one rotation time R of the relative rotation and the velocity V of the relative linear movement.

In the X-ray CT apparatus in accordance with the thirteenth aspect described above, the X-ray CT data acquisition method in accordance with the fourth aspect can be suitably implemented.

In a fourteenth aspect, the present invention provides an X-ray CT in accordance with the thirteenth aspect, wherein when a value obtained by dividing the holding time τ by the one rotation time R of the relative rotation is the amount of table resting T, the amount of table resting T in the case where the velocity V of the relative linear movement is a value V2 larger than a value V1 is set larger than the amount of table resting T in the case where the velocity V of the relative linear movement is the value V1.

The X-ray CT in accordance with the fourteenth aspect, the X-ray CT data acquisition method in accordance with the fifth aspect can be suitably implemented.

In a fifteenth aspect, the present invention provides an X-ray CT apparatus in accordance with the tenth aspect, wherein:

when the area where an image outside the linear movement range from the starting point of the linear movement to the end point of the linear movement can be created is defined as an image extension area, the holding time τ, which is the time spent for acquiring the projection data by performing only the relative rotation without performing the relative linear movement, relies on the width of the image extension area d.

In the X-ray CT apparatus in accordance with the fifteenth aspect described above, the X-ray CT data acquisition method in accordance with the sixth aspect can be suitably implemented.

In a sixteenth aspect, the present invention provides an X-ray CT apparatus in accordance with the fifteenth aspect, wherein the holding time τ2 in the case where the width of the image extension area d is a value d2 larger than a value d1 is longer than the holding time τ1 in the case where the width of the image extension area d is the value d1.

In the X-ray CT apparatus in accordance with the sixteenth aspect described above, the X-ray CT data acquisition method in accordance with the seventh aspect can be suitably implemented.

In a seventeenth aspect, the present invention provides an X-ray CT apparatus in accordance with the tenth aspect, wherein the holding time τ, which is the time spent for acquiring the projection data by performing only the relative rotation without performing the relative linear movement, relies on the one rotation time R of the relative rotation and the width of the image extension area d.

In the X-ray CT apparatus in accordance with the seventeenth aspect described above, the X-ray CT data acquisition method in accordance with the eighth aspect can be suitably implemented.

In a eighteenth aspect, the present invention provides an X-ray CT apparatus in accordance with the seventeenth aspect, wherein when a value obtained by dividing the holding time τ by the one rotation time R of the relative rotation, the amount of the table resting T in the case where the width of the image extension area d is a value d2 larger than a value d1 is set larger than the amount of the table resting T in the case where the width of the image extension area d is the value d1.

In the X-ray CT apparatus in accordance with the eighteenth aspect described above, the X-ray CT data acquisition method in accordance with the ninth aspect can be suitably implemented.

In the X-ray CT data acquisition method and X-ray CT apparatus in accordance with the present invention, the projection data can be positively acquired for reconstructing an image at a slice position outside the linear movement range in the helical scan, helical shuttle, or variable helical pitch scan.

DETAILED DESCRIPTION OF THE INVENTION

Figure 1:
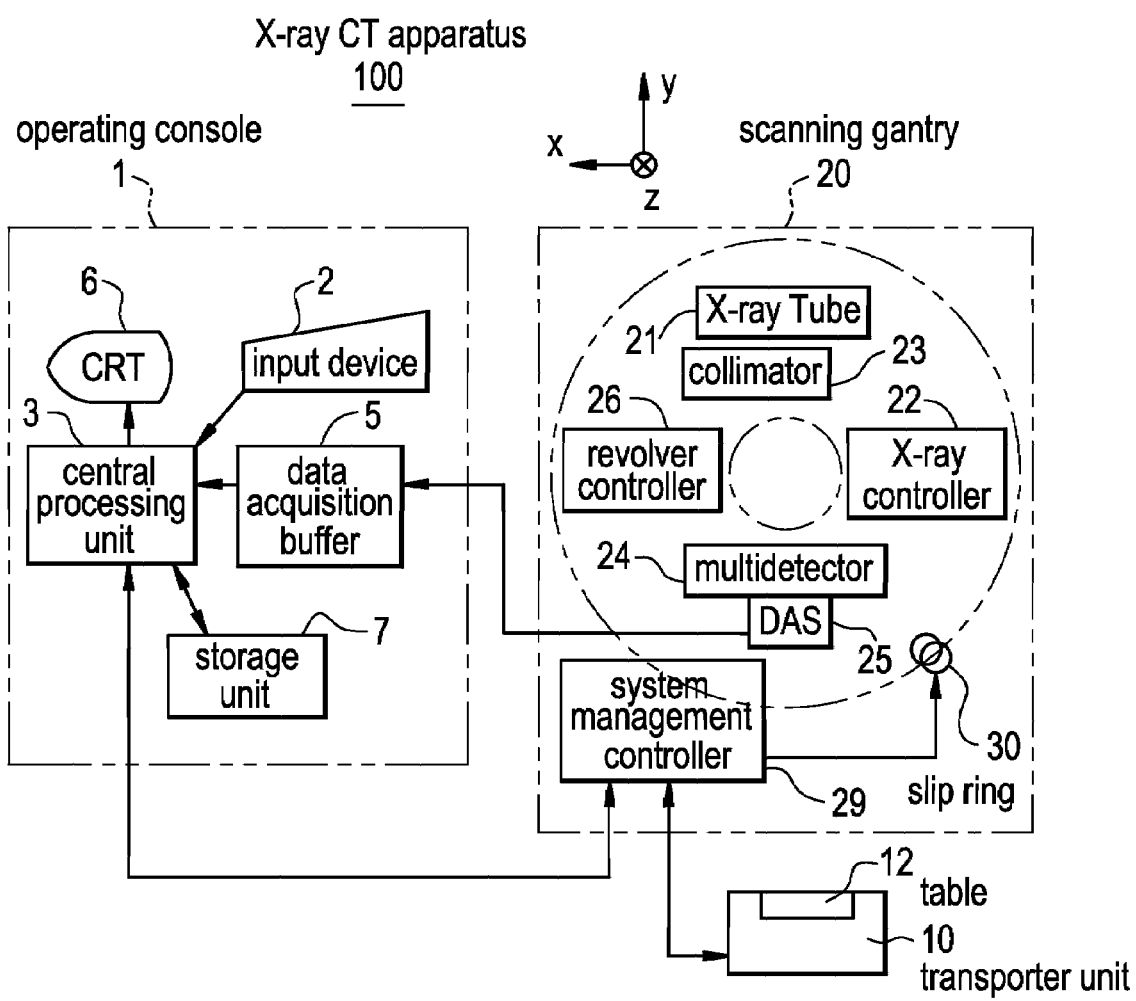
FIG. 1 shows a schematic diagram illustrating an X-ray CT apparatus in accordance with the first embodiment.

The present invention will be described in greater details herein below by referencing some best modes for carrying out the invention as shown in the drawings. It should be noted here that the embodiments disclosed herein is not to be considered to limit the invention.

First Embodiment

Now referring to FIG. 1, there is shown a schematic diagram illustrating an X-ray CT apparatus 100 in accordance with first preferred embodiment of the present invention.

The X-ray CT apparatus 100 includes an operating console 1, a transporter unit 10, and a scanning gantry 20.

The operating console 1 includes an input device 2 for receiving the input from an operator, a central processing unit 3 performing processing such as the image reconstruction, a data acquisition buffer 5 for acquiring projection data obtained from the scanning gantry 20, a CRT 6 for displaying a CT image reconstructed from the projection data, and a storage unit 7 for storing the programs, data, and X-ray CT images.

The transporter unit 10 includes a table 12 to carrying thereon an object to be imaged and carrying in to and out from the bore (central core) of the scanning gantry 20. The table 12 is elevated up and down and translated back and forth by a motor built into the transporter unit 10.

The scanning gantry 20 includes an X-ray tube 21, an X-ray controller 22, a collimator 23, a multidetector 24, a DAS (data acquisition system) 25, a revolver controller 26 for controlling the X-ray controller 22, the collimator 23, and the DAS 25, a system management controller 29 for sending control signals to and from the operating console 1 and the transporter unit 10, and a slip ring 30.

Figure 2:
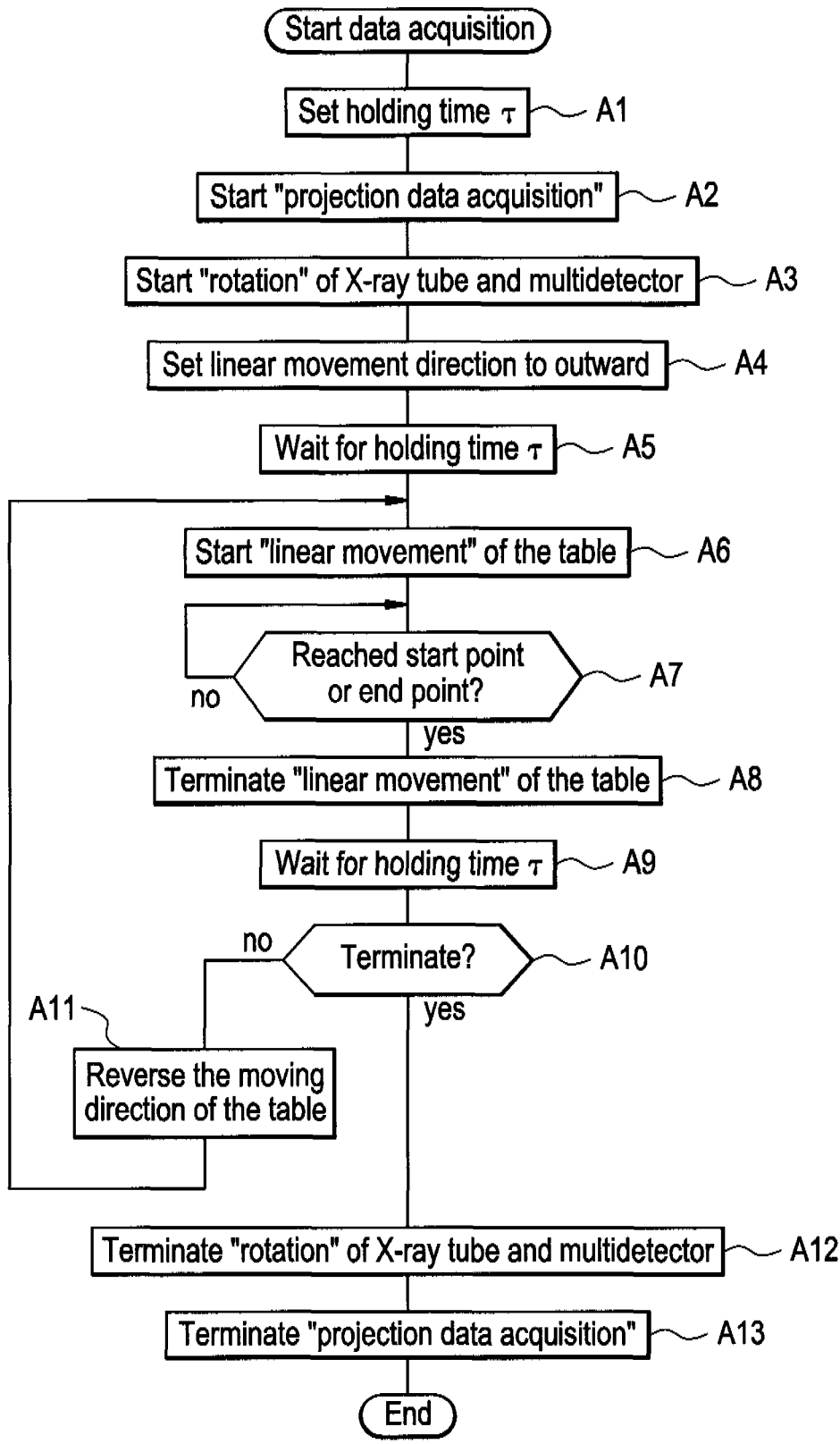
FIG. 2 shows a schematic flow diagram illustrating the data acquisition system in accordance with the first embodiment.

Now referring to FIG. 2, there is shown a schematic flow diagram illustrating the data acquisition process.

In step A1, the holding time $\tau$ is set based on the parameters set by the user as the scanning condition. For example, the holding time $\tau$ is set as follows.

Figure 3:
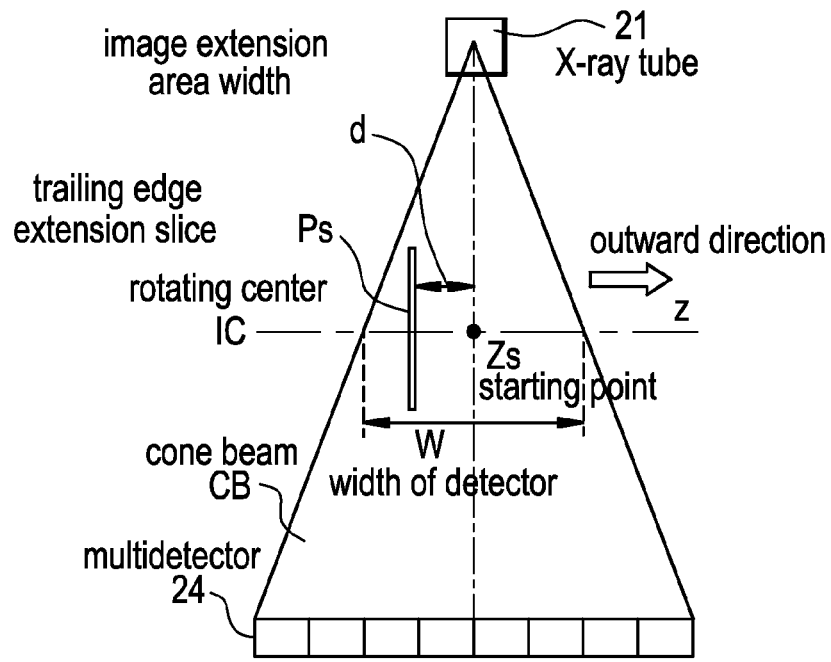
FIG. 3 shows a schematic diagram illustrating the image extension area width d.

As shown in FIG. 3, a width of the image extension area d is assumed in the opposite side of the direction of linear movement (outward direction) from the starting point Zs of the linear movement, and some CT images are desired to be obtained extensively from within the width of the image extension area d. When the width of detector is defined as W, $0 < d \leq W/2$.

After starting the rotation, and after elapsing the holding time $\tau$, the linear movement is started. Now assuming that at the time Tm after starting the rectilinearly movement of the cone beam CB elapsed, the trailing edge of the cone beam CB passes over the position of the trailing end extension slice P, the total elapsed time Tp since starting the rotation will be:

$$Tp = \tau + Tm.$$

When one rotation time is R then the angular velocity will be $2\pi/R$. Therefore, by integrating the angular velocity $2\pi/R$ by the total elapsed time Tp, the revolving angle $\Theta$ during the total elapsed time Tp can be obtained.

$$\Theta = \int_0^{TP} 2\pi/R \cdot dt = \int_0^{\tau+Tm} 2\pi/R \cdot dt$$

The $\Theta$ should be at $2\pi$ in case of full reconstruction, or should be at $4\pi/3$ in case of half reconstruction, thus, $$2\pi = \int_0^{\tau+Tm} 2\pi/R \cdot dt$$

or $$4\pi/3 = \int_0^{\tau+Tm} 2\pi/R \cdot dt$$

By reforming the expression $$1 = \int_0^{\tau+Tm} 1/R \cdot dt \tag{1f}$$

or $$2/3 = \int_0^{\tau+Tm} 1/R \cdot dt \tag{1h}$$

On the other hand by integrating the velocity V during the time Tm, the distance L of linear movement of the trailing edge of the cone beam CB from the position at the start of linear movement to the position of the trailing edge extension slice P can be obtained.

$$L = \int_0^{Tm} V \cdot dt$$

However, the distance $L = (W/2) - d$, therefore $$(W/2) - d = \int_0^{Tm} V \cdot dt \tag{2}.$$

By eliminating Tm from (1f) or (1h) and (2), then the holding time $\tau$ can be calculated.

When ignoring the rotation and the acceleration time during the linear movement, then $$1 = (\tau + Tm)/R \tag{1f'}$$

or $$2/3 = (\tau + Tm)/R \tag{1h'}$$

and since $$(W/2) - d = Tm \cdot V \tag{2'}$$

then $$1 = [\tau + \{(W/2) - d\}/V]/R \tag{1f''}$$

or $$2/3 = [\tau + \{(W/2) - d\}/V]/R \tag{1h''}$$

then transforming $$\tau = R - \{(W/2) - d\}/V \tag{3f}$$

or $$\tau = 2R/3 - \{(W/2) - d\}/V \tag{3h}$$

therefore the holding time $\tau$ can be calculated.

When (3f) can be transformed to yield the amount of table resting T which is obtained by dividing the holding time $\tau$ by the one rotation time R, $$d = R \cdot V \cdot T + W/2 - R \cdot V \tag{4f}.$$

Figure 4:
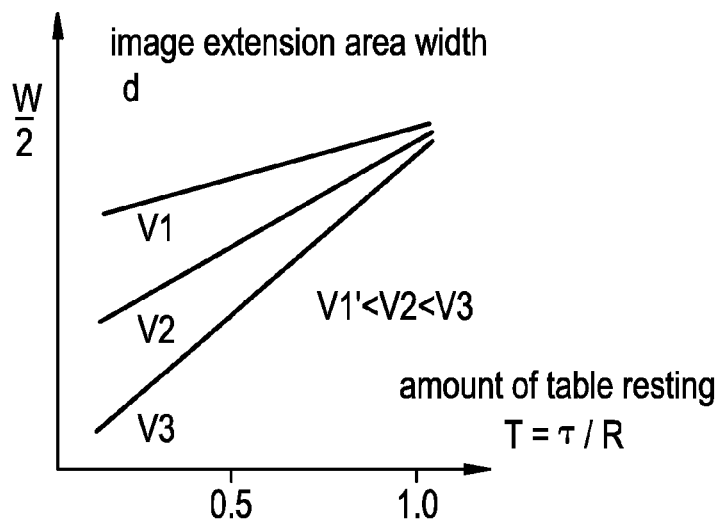
FIG. 4 shows a graph illustrating the relationships between the amount of table resting T=τ/R, the width of the image extension area d, the velocity V, and the holding time τ.

Now referring to FIG. 4, there is shown a schematic conceptual diagram illustrating the expression (4f) when the velocity V1, V2, and V3. Here V1<V2<V3.

Figure 5:
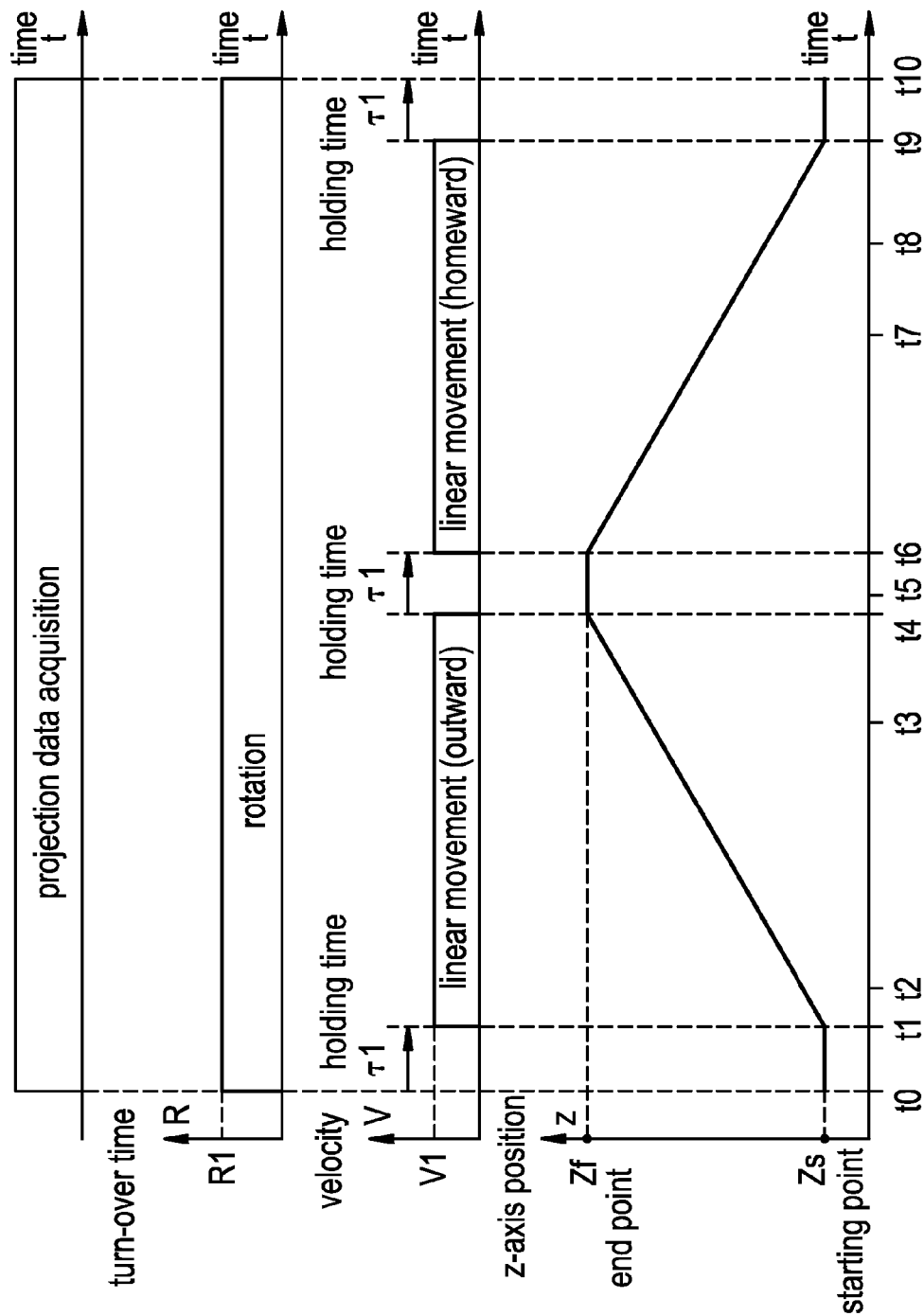
FIG. 5 shows a timing chart illustrating the "projection data acquisition", "rotation", "linear movement", and "the position of the X-ray tube and the multidetector".

Now return to FIG. 2, in step A2, as shown by the time t0 of FIG. 5 for example, the "projection data acquisition" starts.

In step A3, as shown by the time t0 of FIG. 5 for example, the "rotation" of the X-ray tube 21 and the multidetector 24 starts.

In step A4, the linear movement direction of the X-ray tube 21 and the multidetector 24 with respect to the table 12 is set to outward direction (+z direction, in this example).

In step A5, as shown in times t0 to t1 of FIG. 5, the linear movement is held for the holding time $\tau 1$. More specifically the projection data is acquired for the holding time $\tau 1$ with rotation and without linear movement.

In step A6, as shown by the time t1 of FIG. 5 for example, the "linear movement" of the table 12 starts.

In step A7, until for example the table 12 reaches the end point Zf shown in FIG. 5, the projection data is acquired with the rotation and linear movement. At the time when the table 12 reaches the end point Zf shown in the time t4 of FIG. 5, the process proceeds to step A8.

In step A8, As shown by the times t4 of FIG. 5 for example, the "linear movement" of the table 12 terminates.

In step A9, as shown by the times t4 to t6 of FIG. 5 for example, the process waits for the holding time $\tau 1$, in other words, the projection data is acquired by the holding time $\tau 1$ with rotation and without linear movement.

In step A10, If the data acquisition is not terminated as scheduled, then the process proceeds to step A11, otherwise the process proceeds to step A12.

In step A11, the moving direction of the table 12 is reversed. Then the process go back to step A6 to continue the data acquisition. More specifically, by using the end point of the immediately previous run as the starting point of the current run, and the starting point of the immediately previous run as the end point of the current run, the table 12 is translated in the opposite direction to the immediately previous run to acquire the projection data.

In step A12, as shown by the time t9 of FIG. 5 for example, the "rotation" of the X-ray tube 21 and the multidetector 24 is terminated.

In step A13, as shown by the time t10 of FIG. 5 for example, the "projection data acquisition" is terminated.

Figure 6:
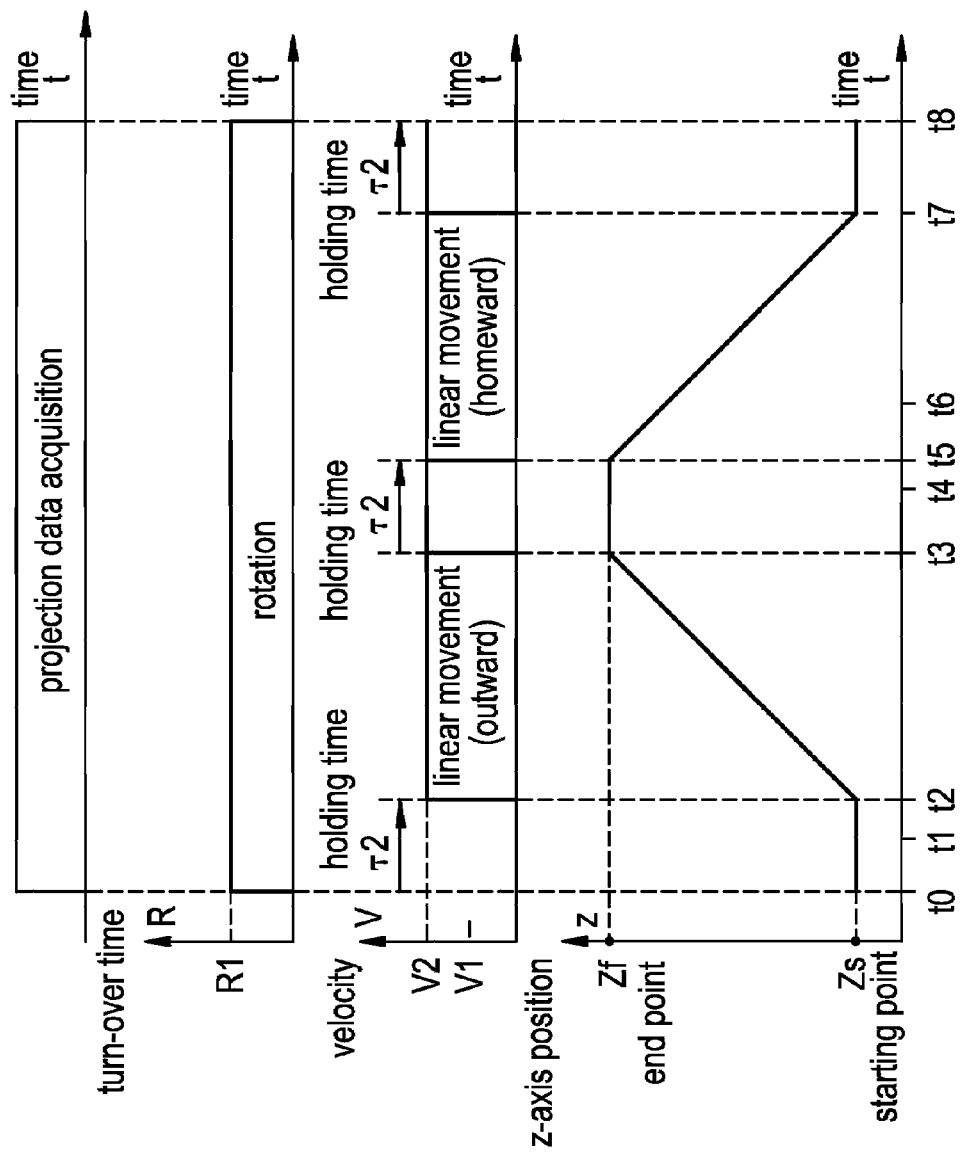
FIG. 6 shows a timing chart illustrating the "projection data acquisition", "rotation", "linear movement", and "the position of the X-ray tube and the multidetector", in a condition that only the velocity V is different from FIG. 5.

Now referring to FIG. 6, there is shown a timing chart illustrating the "projection data acquisition", "rotation", "linear movement", and "the position of the X-ray tube 21 and the multidetector 24" in a condition that only the velocity V is different from FIG. 5.

Since the velocity is V1<V2, then the holding time τ will be τ2>τ1.

Figure 7:
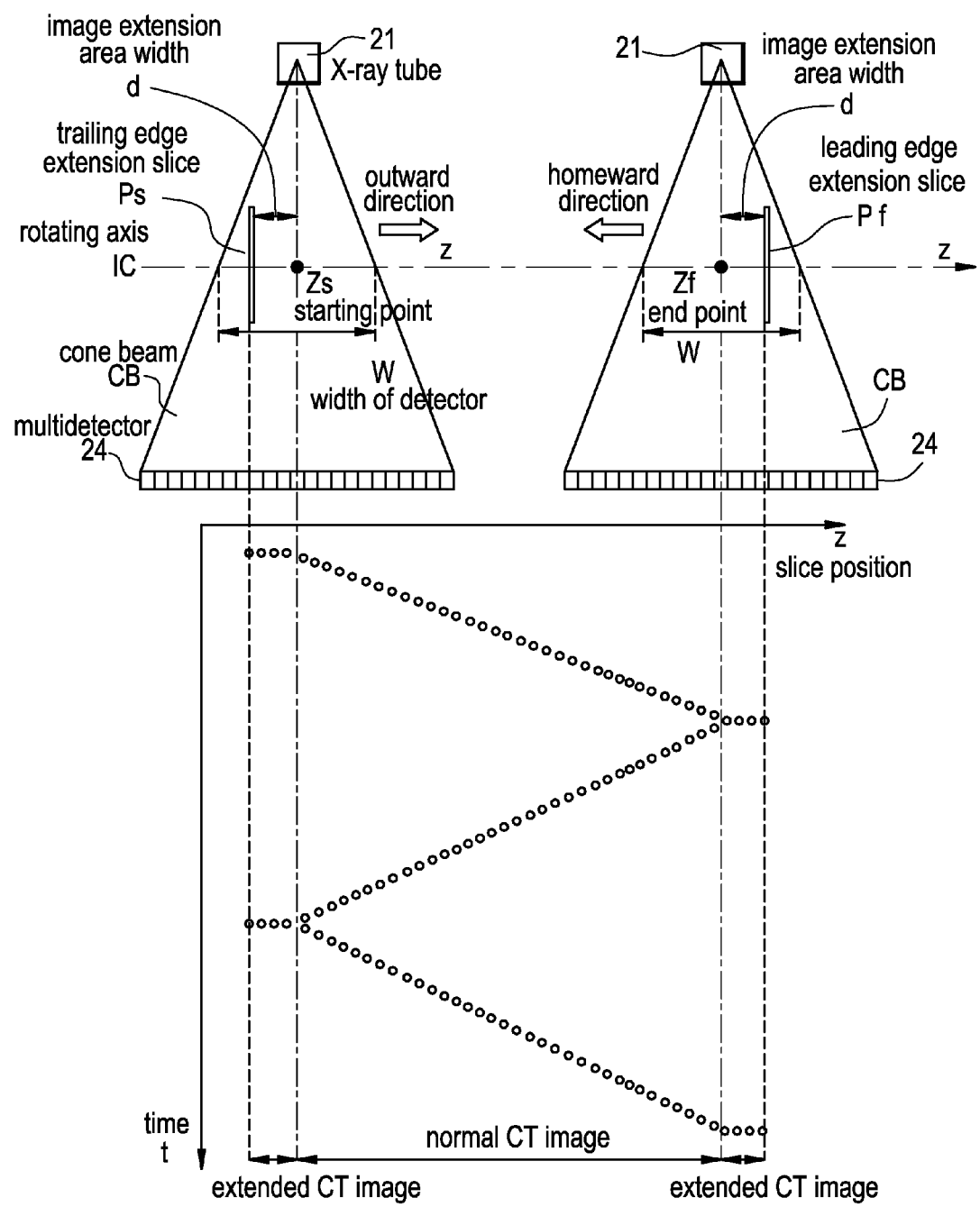
FIG. 7 shows a schematic diagram illustrating the time and the slice position corresponding to the normal CT image and extended CT image obtained when repeating the reciprocation of linear movement.

Now referring to FIG. 7 there is shown a schematic diagram illustrating the time and slice position corresponding to the normal CT image and extended CT image that can be obtained when the reciprocation of linear movement of the X-ray tube 21 and the multidetector 24 is repeated.

In the X-ray CT apparatus 100 in accordance with the first embodiment, the projection data can be positively acquired for image reconstruction of the CT image at the slice position outside the linear movement range.

Second Embodiment

In the first embodiment although a case has been described when the velocity V is varied with the same width of the image extension area d and the same one rotation time R, the holding time τ can be calculated from (1f) or (1h) and (2) in a manner similar to the previous embodiment when the width of the image extension area d is varied, and when the one rotation time R is varied.

The X-ray CT data acquisition method and the X-ray CT apparatus in accordance with the present invention can be used in for example Perfusion CT.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT apparatus, comprising:
an X-ray tube for irradiating a cone beam X-ray;
a multidetector;
a revolving device for relatively rotating around an imaging object at least one of the X-ray tube and the multidetector;
a linear movement device for relatively linearly moving at least one of the X-ray tube and the multidetector from a start point of a relative linear movement to an end point of the relative linear movement with respect to the imaging object;
a scanning device for acquiring projection data by performing only the relative rotation for a holding time τ without performing the relative linear movement at the start point of the relative linear movement and/or at the end point of the relative linear movement and performing the relative rotation and the relative linear movement for a relative linear movement range so as to acquire the projection data to use for reconstructing CT images related to the relative linear movement range and an image extension area, wherein the relative linear movement range is a range from the start point of the relative linear movement to the end point of the relative linear movement and the image extension area is an area created outside the relative linear movement range; and
an image reconstruction device for generating a CT image related to the relative linear movement range and an image extension area by using the projection data acquired.

2. An X-ray CT apparatus according to claim 1, wherein:
the scanning device sets the holding time τ based on a velocity V of the relative linear movement.

3. An X-ray CT apparatus according to claim 2, wherein:
the scanning device sets the holding time τ such that a holding time τ2 in a case where the velocity V of the relative linear movement is a value V2 larger than a value V1 is set longer than a holding time τ1 in the case where the velocity V of the relative linear movement is the value V1.

4. An X-ray CT apparatus according to claim 1, wherein:
the scanning device sets the holding time τ based on a one rotation time R of the relative rotation and a velocity V of the relative linear movement.

5. An X-ray CT apparatus according to claim 4, wherein:
the scanning device sets such that an amount of table resting T in a case where the velocity V of the relative linear movement is a value V2 larger than a value V1 is set larger than the amount of table resting T in the case where the velocity V of the relative linear movement is the value V1, wherein the amount of table resting T is a value obtained by dividing the holding time τ by the one rotation time R of the relative rotation.

6. An X-ray CT apparatus according to claim 1, wherein:
the scanning device sets the holding time τ based on the image extension area d.

7. An X-ray CT apparatus according to claim 6, wherein:
the scanning device sets the holding time τ such that the holding time τ2 in a case where the width of the image extension area d is a value d2 larger than a value d1 is longer than the holding time τ1 in the case where the width of the image extension area d is the value d1.

8. An X-ray CT apparatus according to claim 1, wherein:
the scanning device sets the holding time τ based on a one rotation time R of the relative rotation and the width of the image extension area d.

9. An X-ray CT apparatus according to claim 8, wherein:
the scanning device sets such that an amount of the table resting T in a case where the width of the image extension area d is a value d2 larger than a value d1 is set larger than the amount of the table resting T in the case where the width of the image extension area d is the value d1, wherein the amount of the table resting T is a value obtained by dividing the holding time τ by the one rotation time R of the relative rotation.

* * * * *